US006635015B2

(12) United States Patent
Sagel (10) Patent No.: US 6,635,015 B2
(45) Date of Patent: *Oct. 21, 2003

(54) BODY WEIGHT MANAGEMENT SYSTEM

(75) Inventor: Paul Joseph Sagel, Maineville, OH (US)

(73) Assignee: The Procter & Gamble Company, Cincinnati, OH (US)

(*) Notice: Subject to any disclaimer, the term of this patent is extended or adjusted under 35 U.S.C. 154(b) by 9 days.

This patent is subject to a terminal disclaimer.

(21) Appl. No.: 09/839,740

(22) Filed: Apr. 20, 2001

(65) Prior Publication Data

US 2002/0156351 A1 Oct. 24, 2002

(51) Int. Cl.$^7$ ................................................ A61B 5/00
(52) U.S. Cl. .................... 600/300; 128/903; 128/904; 128/921
(58) Field of Search .................. 600/300, 301, 600/531; 128/921; 705/2, 3; 708/131, 133; 177/245, 264, 25.16; 434/127; 424/439

(56) References Cited

U.S. PATENT DOCUMENTS

| | | | |
|---|---|---|---|
| 4,298,601 A | * 11/1981 | Howard ...................... 424/642 |
| 4,891,756 A | 1/1990 | Williams, III |
| 5,214,966 A | 6/1993 | Delsing |
| 5,673,691 A | * 10/1997 | Abrams et al. ............. 128/921 |
| 5,704,350 A | 1/1998 | Williams, III |
| 5,796,009 A | 8/1998 | Delsing |
| 5,827,180 A | 10/1998 | Goodman |
| 5,828,943 A | 10/1998 | Brown |
| 5,832,448 A | 11/1998 | Brown |
| 5,879,163 A | 3/1999 | Brown et al. |
| 5,897,493 A | 4/1999 | Brown |
| 5,899,855 A | 5/1999 | Brown |
| 5,908,301 A | * 6/1999 | Lutz ........................... 128/921 |
| 5,913,310 A | 6/1999 | Brown |
| 5,918,603 A | 7/1999 | Brown |
| 5,932,812 A | 8/1999 | Delsing |
| 5,933,136 A | 8/1999 | Brown |
| 5,951,300 A | 9/1999 | Brown |
| 5,956,501 A | 9/1999 | Brown |
| 5,960,403 A | 9/1999 | Brown |
| 5,989,188 A | * 11/1999 | Birkhoelzer et al. ........ 128/921 |
| 6,032,119 A | 2/2000 | Brown et al. |
| 6,101,478 A | 8/2000 | Brown |
| 6,168,563 B1 | 1/2001 | Brown |
| 6,207,638 B1 | 3/2001 | Portman |
| 6,210,702 B1 | * 4/2001 | Samman ..................... 424/439 |
| 6,248,065 B1 | 6/2001 | Brown |
| 6,267,988 B1 | * 7/2001 | Meyer ........................ 424/439 |

FOREIGN PATENT DOCUMENTS

| | | |
|---|---|---|
| EP | 0 771 817 A2 | 7/1997 |
| EP | 0670064 B1 | 8/2001 |
| WO | WO 00/32098 A1 | 6/2000 |
| WO | WO 00/52604 A1 | 9/2000 |
| WO | WO 01/26535 A2 | 4/2001 |
| WO | WO 01/28416 A1 | 4/2001 |
| WO | WO 01/39089 A1 | 5/2001 |
| WO | WO 01/52718 A2 | 6/2001 |
| WO | WO 01/89365 A2 | 11/2001 |

* cited by examiner

Primary Examiner—Eric F. Winakur
Assistant Examiner—David J. McCrosky
(74) Attorney, Agent, or Firm—Kelly L. McDow-Dunham; John M. Howell (57) ABSTRACT

The invention relates to body weight management systems for subjects including humans and domestic animals. Such systems utilizes devices and compositions to shift the energy balance of the user in the direction wherein the calories burned due to the user's activity is greater than the calories consumed by that user. These devices include a diet-tracking system, devices for estimating energy expenditure of the subject and a satiety agent. Such systems have a variety of uses including, but not limited to body weight maintenance, reduction or gain; reduction of body fat and, or gain in muscle mass and improvement of a subject's fitness.

17 Claims, 8 Drawing Sheets

BODY WEIGHT MANAGEMENT SYSTEM

FIELD OF THE INVENTION

The invention relates to body weight management systems for subjects including humans and domestic animals. Such systems utilize diet-tracking systems, devices to measure energy output and compositions comprising satiety agents. Such systems are used by subjects to assist the subject in terms of making choices in terms of exercise and, or the consumption of foods, beverages and other nutritional products in order to remain on target for meeting their desired body shape, weight, and fitness level goals. The system can be used by the subject's care-giver or alternatively by the subjects themselves. The system may also be interactive.

Definitions:

"Authenticating Code"

Any form of identification provided by the subject to verify the authenticity as a subscriber to the body weight management system when attempting to access said system. Said authenticating code includes, but is not limited to a Personal Identification Number or PIN.

"Body Weight Management"

Managing a subject's body weight gains, losses and maintenance of a desirable weight, the fat to muscle ratio, fitness or physical condition, body appearance or shape and all combinations thereof.

"Carbon Dioxide Scrubbing System"

A system associated with indirect calorimetry that is designed to absorb carbon dioxide from respiratory gases for the end purpose of determining the volume of oxygen used by the subject.

"Computing Device"

Any programmable electronic device having sufficient memory capacity to store, retrieve and, or process data.

"Database"

Accessible accumulated information regarding foods and their nutritional value including caloric content attributed to particular elements making up the foods (fats, carbohydrates, fiber and the like); energy expenditure value estimates for specified physical activities including, but not necessarily limited to various exercises; data from diet-tracking system; data from activity monitoring device, calorimeter and any other data or information relevant to supporting a subject's body weight management goals and, or fitness.

"Data Processor"

Devices and, or electrical components capable of converting raw data to machine readable form and subsequent processing such as storing, updating, calculating, rearranging, manipulating or transferring data or information. This includes the computing device, physical activity monitor, calorimeter and, or a stand alone external equipment managed by the system provider.

"Direct Calorimetry"

The determination of heat produced by an individual during his or her bodily processes.

"Electronic Transmission"

The transfer or movement of data or information via radio frequency, optical, digital, either using hard wire or wire-less means.

"Energy Balance"

The relationship between the intake of calories attributed to the foods consumed by a subject and the number of calories expended or burned by the subject during daily physical activities.

"Foods"

All consumables including food stuffs, beverages and other substances or products that are capable of producing energy in the form of heat, otherwise referred to as calories.

"Hand Held Programmable Device"

A portable device with sufficient memory capacity to record and process the data, transferring the results for electronic transmission to the weight manager for analysis and optionally provide feedback to subject.

"Network Site"

Any system providing communication of information and, or data between at least two subjects, at least one subject and a remote communications system or computer, or between two or more computers, data managers, or communication systems.

"Indirect Calorimetry"

The determination of an individual's oxygen utilization at rest and at steady state exercise conditions wherein the anaerobic energy yield is very small and disregarded under such conditions.

"Metabolic Rate"

An individual's total daily energy expenditure including the resting metabolic rate, the thermogenic influence of food consumed and the energy expended due to activity above one's resting state.

"Network Provider"

An entity providing access to electronic communication systems, such as the Internet, for the purpose of conducting electronic communication.

"Non-electronic Recording"

A system for documenting events without using devices to create a electronic record of said events in a medium capable of recording such electronic record.

"Physical Activity Monitor"

Any device measuring the actual or estimate of a subject's energy expenditure due to the subject's activities that consume calories including, but not necessarily limited to motion during physical activities such as work and exercise and other activity undertaken by the subject.

"Portable Media"

Any tangible information source medium capable of being transported from one location to another that can be read, sensed or inferred by the receiving person and, or device. Examples include magnetic recording tape, compact discs, written journals or logs, electronic memory devices such as memory sticks and the like.

"Resting Metabolic Rate"

The minimum level of energy required to sustain the body's vital functions in the waking state at rest.

"Subject"

The individual(s) or animal(s) directly benefiting from using said body weight management system regardless whether said system is administered by the individual or in their behalf of the individual or animal by another. For purposes of this invention, the terms "subject" and "user" are synonymous.

"Subject's Data Profile"

This is the subject's personal information that is a combination of body mass index (weight, height and age), psychological, emotional and social aspects of the subject as well as the subject's body weight management goals.

"Weight Analysis System"

Any method that evaluates the change in a subject's weight as a result of determining the subject's actual or estimated energy either qualitatively or quantitatively using non-electronic means, software, or web based means, or review of diet tracking and energy expenditure logs and, or records and mixtures thereof.

"Weight Manager"

Any person, device and combinations thereof that uses analytical and, or diagnostic processes to analyze data for the purpose of providing feedback relating to body weight management by control of a subject's energy balance including energy intake and energy expenditure of a subject.

"Weight Management System Provider"

The person, company or organization supplying services, data bases and, or information processing needs as well as support software for the subjects to access said system.

BACKGROUND OF THE INVENTION

In developed countries around the world, there is a tremendous interest in personal fitness and wellness. At the same time there is a disturbing trend that people, including adults and children and domesticated animals or companion animals are becoming overweight. By overweight, it is meant that the subject has exceeded acceptable weight range and percent body fat generally considered as healthy determined by factors including, but not necessarily limited to age, height, sex, and body type. For example, over 50% of the human population in the United States is considered overweight, approximately 20% being obese. Obesity produces a wide range of health concerns including sleep apnea, orthopedic complications, arterial sclerosis, diabetes and heart disease. All these undesirable conditions contribute in development of an unsatisfactory quality of life and in some cases premature death.

Many studies have been conducted to identify the factors that contribute to being overweight. The main factors include high caloric density in foods, large portion sizes, diets that are rich in fat, decreasing amounts of exercise, high availability of food, increased numbers of eating occasions, low knowledge of actual foods and portions eaten by the consumer, lack of information on energy expenditure through normal daily activities and exercise, and eating stimulated by stress, hormonal shifts during the menstrual cycle for women, and hunger. A number of approaches to control the caloric balance including consumable products have been developed with mixed success. In the United States, over the counter weight loss products are sold to help consumers reduce their weight or maintain current weight. These products are grouped into over the counter diet aids and meal replacements. The over the counter diet aids include appetite suppressants, like Dexatrim® and Acutrim®, which both use phenylpropranolamine as the appetite suppressant. This appetite suppressant can even be released over time to help control hunger for longer periods of time for the consumer. In addition, there are dietary supplements, like Metabolife 356®, which help people with their diets while providing energy. Consumers use these products up to 3 times a day to help control hunger and increase energy.

Meal replacement products include examples like Slimfast®, Ensure®, Boost® and other products which contain a blend of nutrients for use as a snack or replacement of high calorie meals. They are offered in a variety of forms, such as liquid shakes, solid bars, pastries and other savory forms.

There are also prescription drugs that can help consumers to lose weight that fall into the anti-obesity drug class. These drugs are used to decrease appetite or increase the feeling of being full by possibly increasing levels of serotonin or catecholamine—two brain chemicals that effect mood and appetite. Examples of products in this group include Fastin® from Smith-Kline-Beechan which uses phentemyne hydrochloride, Meridia® from Knoll-BASF Pharma which uses sibutramine and Pondimin® from Wyeth Ayerst which uses phenfloramine hydrochloride. Redux® from Wyeth Ayerst uses dexfenfluramine. All of these products must be obtained through a physician by use of a prescription.

There are also commercial weight loss programs available through programs like Weight Watchers®, Jenny Craig®, and hospital supervised programs that are designed to help consumers track energy intake and energy output through a variety of techniques and devices. While many of the technologies mentioned above are useful in losing weight, the problem is keeping the weight off. Often people "yo-yo", that is, lose large amounts of weight only to gain it back once they get off the weight loss program they were on.

It is believed that the more effective body weight management approaches have three primary elements: measuring energy intake in the form of calories eaten, measuring energy expenditure of the body and managing hunger or creating a feelings of fullness or satiety without actually consuming a foods. The combination of these three elements provides consumers with a good measure of the energy intake that their body needs versus what they are actually providing with the food they consume that results in energy balance or imbalance relative to intake and expenditure.

BRIEF DESCRIPTION OF THE INVENTION

The present invention is a novel system for subjects to effectively manage a subject's energy balance for meeting the subject's desired body shape, weight, and fitness level goals. The body weight management system for self-management of said subject's body weight comprises a diet-tracking system for estimating the subject's individual energy intake or caloric intake over a set period of time; devices for estimating the energy expenditure of the subject and compositions comprising satiety agents selected from the group consisting of long chain fatty acids, their non-glyceryl esters, hydrolyzable in the presence of gastrointestinal enzymes, and mixtures thereof, wherein said satiety agent releases in the stomach.

The subject collects data regarding his or her calories attributed to their eaten foods and the energy expenditure in calories. When the energy intake and the energy expenditure are about the same, the subject experiences no net body weight gain. If a subject routinely consumes more calories than they can expend or "burn" over an established period of time, the subject gains body mass or weight. To lose weight, the balance is shifted in the direction wherein the energy expenditure is greater than energy intake through the food consumed. In addition, the subject consumes satiety agents to curb their appetite shifting the energy balance in favor of energy expenditure. This may be done over a period of time, providing a reliable and safe means for reducing one's weight. This system can be employed even after losing the desired weight to maintain their desired body weight or mass.

DETAILED DESCRIPTION OF THE INVENTION

Diet-Tracking System

The caloric intake by the consumer is determined by diet-tracking systems. These systems can be manual tracking systems wherein the user maintains a log of the foods consumed over a set period of time and calculates the caloric intake over a period of time. Such a log can be in written form using simply a note pad and a pencil or pen. More elaborate commercial diet-tracking systems may also be used in the present invention. Such systems typically are divided into daily periods and are designed to log the foods eaten, often from specified food groups and a place to document the calories associated with the foods consumed.

Example of such systems include the record keeping system as described in "Mayo Clinic on Healthy Weight," edited by Donald D. Hensrud, © 2000. The Mayo Clinic discloses using the Health Weight Pyramid wherein the user is to check off the boxes within the pyramid to indicate consumption of foods from categories including vegetables, fruits, carbohydrates protein/dairy and fats. On the basis of the number of calories allowed per day, there are established recommended levels of each category of foods that may be consumed. The goal is to meet these restrictions and record the actual foods eaten per day.

The Life Exercise Attitudes Relationships Nutrition, Master Monitoring Form, created by Kelly D. Brownell, © 2000, American Health Publishing Company, Dallas Tex. This system comprises a 7-day log to account for the daily food consumption, a column to log in the caloric intake from said food, the food groups from where the calories came, personal goals for that day and, a person's physical activity.

Slim Down Express' 21-day slim down program includes an "Lean Living Organizer" in the form of an appointment book designed to be carried with the individual through the day. The journal includes cues when to eat to avoid going too long between meals without eating. Also included are exercise icons to remind the user to exercise and for what duration. The journal also has a Slim Down Bar icon that shows the best time to consume the system's own meal substitute.

Weight Watchers provides a program where the user keeps a journal of the foods consumed. The journal is similar in approach to those systems previously mentioned. The user logs his or her consumption in terms of the points attributed to the consumed food. Points correspond to the calories, dietary fiber and fat content per serving of the specified food. A person personal daily food point allowance depends on their current weight. The more you weigh, the more food points you need to lose weight at a safe rate. Points can be "banked" from day to day. That is if you eat less than your point allowance for a particular day, you can eat that many more points beyond another day's point total.

Systems have also been developed wherein a person does not have to actually record the calories or points they consume. The Richard Simmons "Food Mover" is a system wherein a user inserts a card into plastic case or "Food Mover." The card, having food group icons printed on it face, is inserted into a slot on the case. The printed icons line up with the window boxes inside the case. As the user consumes one portion of the food group as noted in a companion manual, the user closes that window. This provides a graphic illustration of the daily consumed and yet-to-be consumed foods for a particular day.

Alternative approaches for diet tracking comes by way of electronic systems involving computer tracking software loaded onto a computing system. An example of software useful in the present invention includes Diet Log™, available from SoftCare Clinical Informatics. Such software acts as a personal diet manager for the user. Features of such software generally include a means for automatically calculating the calories resulting from the consumption of food by simply clicking on food icons representing the food eaten. The caloric intake is automatically added and compared with pre-established calorie consumption goals. The software generally includes other features such as customized diets for the user in order to meet their weight loss goals. Additional features include an exercise log. The advantage of using software is the automated features in terms of calculating calories and comparing to established goals and the quick feedback to the user regarding their likelihood they'll meet their weight reduction goals.

The computing system includes any type of a programmable computer and, or hand held device such Palm Pilot™. In case of the later, the user can personally carry it around with them to record foods as they eat them, avoiding laborious logging into a journal or worse, forgetting to account for the food. The information stored in the hand held device can be down loaded to a personal computer or sent directly to an individual's data base over the Internet. The software also generates data that can be electronically relayed or shared with others by traditional means of communication as well as electronic mail and, or use of the Internet. Such user feedback by said manager enables individualized advice to the consumer.

Energy Expenditure Measuring Devices

The energy expenditure half of the above mentioned energy balance is measured using devices including those that detect the amount of heat generated by the body, intensity of cardiac load by measuring heart rate and respiration or the amount of oxygen consumed, as well as electromyography of muscle activity throughout the body. These devices are largely electronic sensor-based devices that detect the rate of metabolism or energy use by the subject's body. These devices include calorimeters, and physical activity monitors including, but not limited to accelerometers, pedometers and other physiologic measures of energy consumed performing daily physical activities.

Calorimeters are devices that measure energy expenditure are well known in the art and include direct and indirect calorimetry. While direct calorimetry is the more accurate, it's not practical and indirect calorimetry is the method most widely applied. Indirect calorimetry devices determine the calories expended as a function of oxygen consumption. These devices utilize algorithms based on known equations wherein the oxygen consumed is determined by measuring both the oxygen consumed and the carbon dioxide produced. The difference between these two levels translates to the rate of consumption of oxygen by the subject or the subject's respiratory quotient. The respiratory quotient can then identify the source of energy that is being utilized by the body, such as protein, fat, carbohydrate and mixtures thereof. It is generally accepted that a liter of oxygen consumed corresponds to 4.8 kilocalories of energy generated or expended. U.S. Pat. No. 3,523,529, Kissen, issued Aug. 11, 1970, discloses polargraphic oxygen sensor to provide an electrical signal proportional to the change in the percentage of oxygen in the inhaled air to that in exhaled air. This measures the amount of oxygen consumed by a subject. U.S. Pat. No. 5,060,656, Howard, issued Oct. 29, 1991, discloses metabolic rate analyzer comprising a flow-proportioning valve for producing a proportional sample of the expired gas of the subject. This provides valuable information relating to the physical condition of the subject, including cardiovascular fitness of the subject.

U.S. Pat. No. 5,503,151, Harnoncourt et al., discloses respiratory gas measuring devices having an ultrasonic sensors contained in a disposable respiration pipe with re-usable per-amplifier circuit contained in a separate housing to avoid contamination after repeated use among subjects. U.S. Pat. No. 5,836,300, Mault, issued Jan. 13, 1999 discloses a respiratory gas analyzer wherein the bi-directional flow meter generates and a capnometer sensor interconnected between mouthpiece and source of respiratory gases. Electrical signals are generated representing the volume of gases passing through the flow meter in either direction.

The output from the data recorded by such devices, otherwise known as the total metabolic rate during a period of time when activity is undertaken, is particularly useful in determining the resting metabolic rate of the subject. This information is combined with the data generated by a physical activity monitor to estimate the energy expenditure of the subject.

Where a subject must understand their total caloric burning rate, a physical activity monitors to estimate the energy expenditure of a subject. While tables are available for subjects to approximate caloric burn values for various physical activities, variation of a number of factors including duration and intensity of the activity limit the usefulness of such charts. Devices have, therefore, been developed to allow an individual to determine the calories burned during exercise. The most effective fitness monitoring devices are those that effectively provide the user with physiological information concerning their exercise level while at the same time providing empirical information with respect to the duration and extent of a workout.

The basis of the calorie burn estimation is the monitoring of the activities of the user. The activity monitoring is derived from odometer readings, pulse meter pedometer readings and exercise machine time/calorie counters. For example, U.S. Pat. No. 4,159,416 to Brajnik et al. disclose a monitor in the form of a wristwatch capable of converting the wearer's pulse to determine the user's number of calories expended. In light of pulse conversion being considered relatively inaccurate, other devices have been developed. These include belt or pocket-worn device that measure the individual's caloric output and continuously accumulates expended calories; see U.S. Pat. No. 4,192,000 to Elmer P. Lipsey.

In order to measure the walking or jogging distance covered by a user, both mechanical and electronic pedometers have been developed. Typically, such pedometers are worn on the side of the user such as by being clipped to a belt or the waist line of the user's pants in the manner of a pager or the like. Other known pedometers are built into a wristwatch worn on the user's wrist. In general, the pedometer functions to record the distance covered by the user by responding to the user's body motion at each step. Pedometers include various features and functions such that they can be adapted to the personal stride of the user. The pedometer may include a display, such as an LCD or LED display, for displaying the distance covered, number of steps taken during the workout, stopwatch and clock features, etc. The pedometer alternatively can interface with another device, such as a computer, for display of the desired information on the computer's screen.

In most cases, the known pedometers use a mechanical sensing device to respond to the user's body motion at each step. However, the use of the mechanical sensor is disadvantageous as it is more susceptible to breakage and inaccuracies. Electronic pedometers are also known which include an electronic sensor circuit to respond to the user's body motion at each step or stride. These electronic pedometers are more reliable and less susceptible to breakage.

While the known pedometers provide useful information during a workout, they unfortunately do not provide the user with any indication as to the level of exertion being placed on the user's body. Thus, while specific performance limitations may be indicated, the pedometer cannot inform the user whether they are training above or below the recommended level. The user therefore needs some indication of the degree of physical effort actually exerted as measured by physiological signs. The use of physiological signs provides a more direct indication to guide the exercise than the information provided by the known pedometers such as the distance traveled, amount of time involved and, or the physical work load.

In view of the above, heart rate monitors in combination with a pedometer have been developed to allow a person to consistently engage in an appropriate quantity and quality of exercise by monitoring the cardiovascular system via the heart rate. In general, effective aerobic conditioning requires that one's heart rate is maintained at a proper level or "target zone" for at least fifteen minutes. Prior to the use of heart rate monitors, a person would have to interrupt the workout in order to manually check their heart rate before continuing or modifying the exertion level of their workout. Of course, the sudden interruption of a workout to check the heart rate is itself disadvantageous.

One known method of monitoring the heart rate uses electrodes attached to the user in the vicinity of the heart.

Electrical signals detected by the electrodes are transmitted via conductors or wires to a processor that can compute the heart rate. These "wired" heart rate monitors present various problems in that the wires often interfere with an exercise workout, particularly during running or walking workouts. They are therefore not particularly suited to active exercising.

There have also been developed so-called "wireless" heart rate monitors that use a telemetric transmitter unit for wirelessly transmitting electrical signals detected by electrodes to a separate receiver device. One such telemetric transmitter unit is described in U.S. Pat. No. 5,491,474. It is also known to use wired or telemetric wireless heart rate monitors with stationary exercise devices such as a cycle ergometer as described, for example, in U.S. Pat. No. 5,456,262. The ergometer is used to simulate an exercise program. However, such combined devices restrict the user's exercise routines to stationary exercise units.

Pedometers have also been developed which incorporate pulse meters for sensing the user's heartbeat, such as in U.S. Pat. No. 5,539,706. In contrast to heart rate monitors that determine the heartbeat in beats per minute (bpm) based on electrical signals from the heart, the pulse meters calculate the heartbeat by sensing blood flow through the user's veins. Typically, pulse meters incorporate an infrared light sensor that is pressed against the user's fingertip or clipped against the user's ear. The infrared light sensor determines how fast the user's blood is pumping through their veins. Unfortunately, such pulse meters encounter problems in that if the user's finger is pressed too hard against the sensor, the blood flow will slow down. By contrast, if pressed too lightly against the sensor, then even the slightest movement of the user's fingertip can give erratic readings. Similarly, the ear-clip pulse meter models can also provide faulty readings due to poor circulation in the user's ears, or to sensor movements caused by the connecting wires that must dangle from the sensor. While the use of pulse meters is accurate when the user remains very still, they become unstable and inaccurate during a fitness routine. This therefore defeats the purpose of using the pulse meter to determine the user's heartbeat during exercise. Proper use of heart rate measurement requires that the user be aware of the heart rate during the exercise. As noted above, however, accurate readings with the pulse meters are accomplished by interrupting or slowing down the exercise routine, which has its own disadvantages notwithstanding the fact that the user's heart rate instantaneously lowers during a stoppage or slow down.

Devices measuring total energy expenditure may also be employed in the system of the present invention. Such devices have the capability to measure the total expenditure of the subject. These devices integrate microprocessors and sensors in a compact device that can be inconspicuously, such as under clothing. For example, BodyMedia developed the SenseWear™ health monitor that is worn around the anterior of the upper arm. This monitor measures a group of specified physiological signals that through a series of algorithms estimates the total energy expenditure of the subject.

Any one or combination of these devices can be used to measure the energy expenditure of the human body. From the earliest to the current devices, technology advances have improved reliability due to the numerous parameters of the individuals and the conditions under which the device is used. Advances have also been made regarding the portability of the devices and the simplicity of their use. These advances have now made such devices affordable to even the individual.

Satiety Agents

A subject can expect to lose about 1 pound of body weight for each 3500 kilocalories deficiency achieved by dieting. A satiety aid taken can assist a subject in avoiding eating due to excessive hunger. Other products that can be used include metabolism stimulators such as caffeine, ephedrine, and other products and ingredients identified in the previous paragraphs. It is the unique combination of knowing what your energy balance is in combination with products that help control eating due to hunger, stress, or other emotional factors that provide consumers with a new way that is uniquely suited to helping them lose weight.

In additional to the foods and beverages normally associated with a user's diet, the present system envisions use of various agents and the products containing such agents can assist the subject manage their hunger, feel full, and increase metabolism. These agents include satiety agents so that with routine use, the subject can manage to his or her advantage the energy intake and expenditure balance necessary to meet their body weight management goals.

The satiety agent utilized in the present system are selected from the group consisting of long chain fatty acids, their non-glyceryl esters, hydrolyzable in the presence of gastro-intestinal enzymes, and mixtures thereof, wherein said satiety agent releases in the stomach. Said satiety agents are disclosed in co-pending patent application U.S. Ser. No. 09/603,626, filed Jun. 26, 2000, assigned to the Procter & Gamble Company and herein incorporated by reference. Specifically, said satiety agents are selected from the group consisting of long chain fatty acids, their non-glyceryl esters, hydrolyzable in the presence of gastro-intestinal enzymes, and mixtures thereof, wherein said satiety agent releases in the stomach. The long chain fatty acids and their non-glyceryl esters contain from about 12 to about 24, preferably from about 16 to about 18 carbon atoms. The carbon chain has from 0 to about 6, preferably from 0 to about 3 carbon-carbon atom double bonds. The fatty acids are selected from group consisting of lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, eicosapentaenoic acid, behenic acid, erucic acid, docosahexaenoic acid, lignoceric acid, and mixtures thereof. Preferred fatty acids are selected from the group consisting of oleic acid, linoleic acid and mixtures thereof.

Non-glyceryl fatty acid esters include, but are not limited to alcohol esters wherein said alcohol portion of the ester is selected from the group of alcohols consisting of methanol, ethanol, n-propanol, isopropanol, n-butanol, isobutanol and mixtures thereof, preferably ethanol. Preferred non-glyceryl fatty acid esters are selected from the group consisting of ethyl oleate, ethyl linoleate and mixtures thereof.

The satiety agent is administered at a time concurrent with food consumption, prior to food consumption, as replacement for food consumption and combinations thereof. Consuming such compositions produces a sensation of satiety wherein the amount of food subsequently consumed is managed. Said satiety agents comprise long chain (greater than 10 carbons) non-esterified fatty acids, their non-glyceryl esters, hydrolyzable in the presence of gastro-intestinal enzymes, and mixtures thereof in compositions that release said satiety agent in the stomach reduces total caloric intake.

This satiety agent may be administered in a wide variety of product forms including non-enteric pharmaceutical dosage forms such as compressed and molded tablets, hard gelatin capsules, soft elastic gelatin capsules, and microcapsules that dissolve in the stomach, emulsions, and suspensions, or as part of a beverage or solid food product. The latter may be used as a meal supplement or replacement. The compositions are administered at a time prior to subsequent consumption of food so as to induce a sensation of satiety in the subjects for a sufficient time wherein the amount of food subsequently consumed is reduced, thus reducing total caloric intake by controlling the subject's appetite. This is believed to be an effective body weight management tool.

Figure 1:
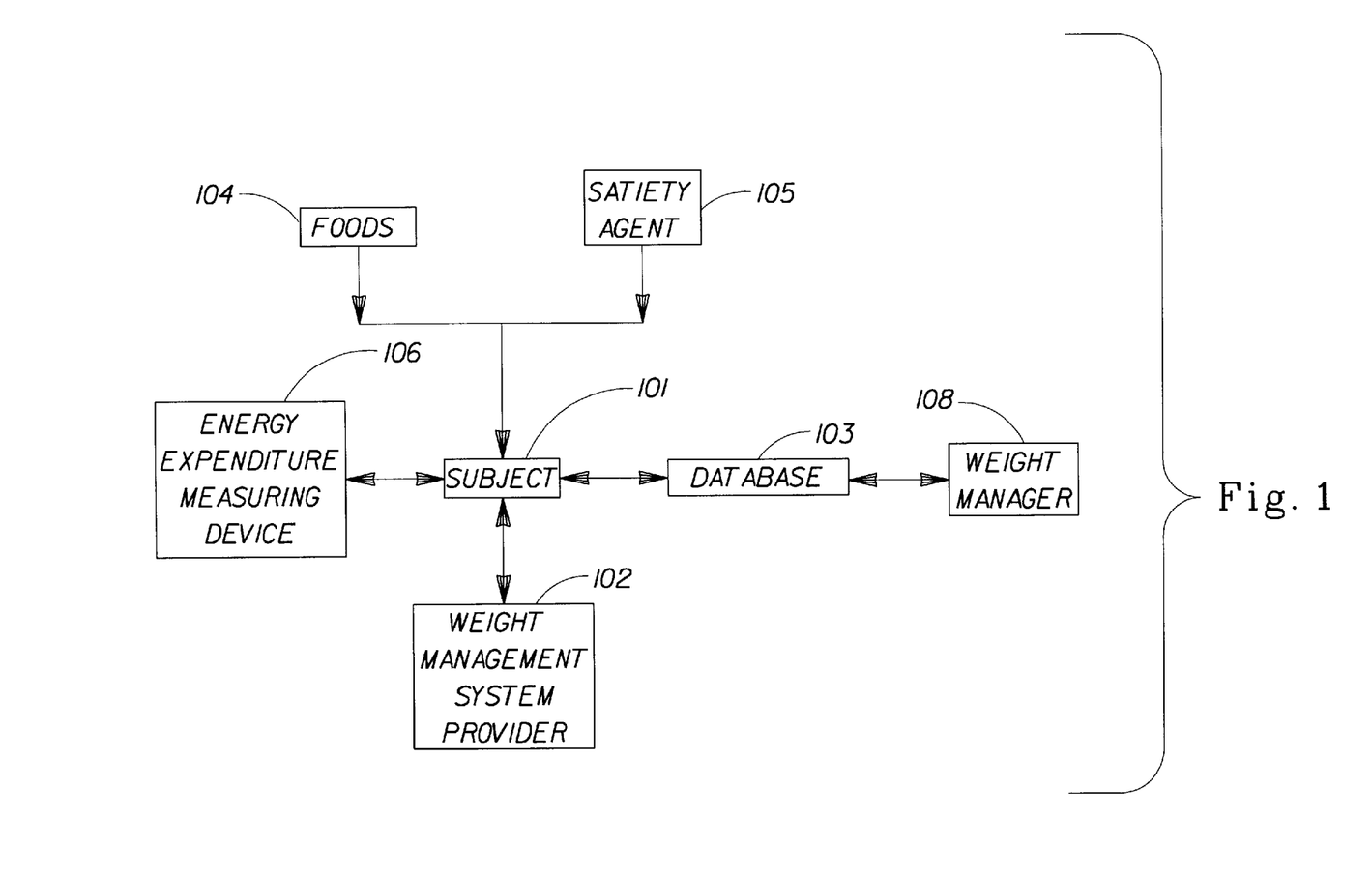
FIG. 1 shows a body weight management system of the present invention wherein the diet-tracking system comprises non-software based subject journal or log. Information is entered into a database. The weight manager is either integral or separate from said database.

FIG. 1 shows the diagram of an embodiment of the body weight management system of the present invention. Body weight management system 100 is where subject or user 101 initiates the system by subscribing to body weight management system 100 through a subscription through the weight management system provider 102. Subject 101 may utilize any of a plurality of communication means to register with said provider 102. Said communication means includes, but is not limited to traditional mail and telephone services. Said system provider 102 transfers body weight management system tools to subject 101. These tools include a diet-tracking system containing a database 103 in the form of a journal to record consumables such as foods 104 to estimate energy input. Other tools sent to subject include satiety agents 105 and energy expenditure measuring device 106. Subject 101 creates a subject data profile in database 103. Subject 101 records the energy intake in the form of foods as well as the satiety agent 105 consumed. The energy expenditure data from the energy expenditure-measuring device 106 is also recorded in the database's journal. The database's journal information is conveyed to a weight manager 108. Said weight manager 108 analyzes said data and generates feedback to be provided to subject 101. The feedback provides subject 101 help in modifying her energy balance factors to maintain progress towards the body weight management goals established in the subject data profile.

Figure 2:
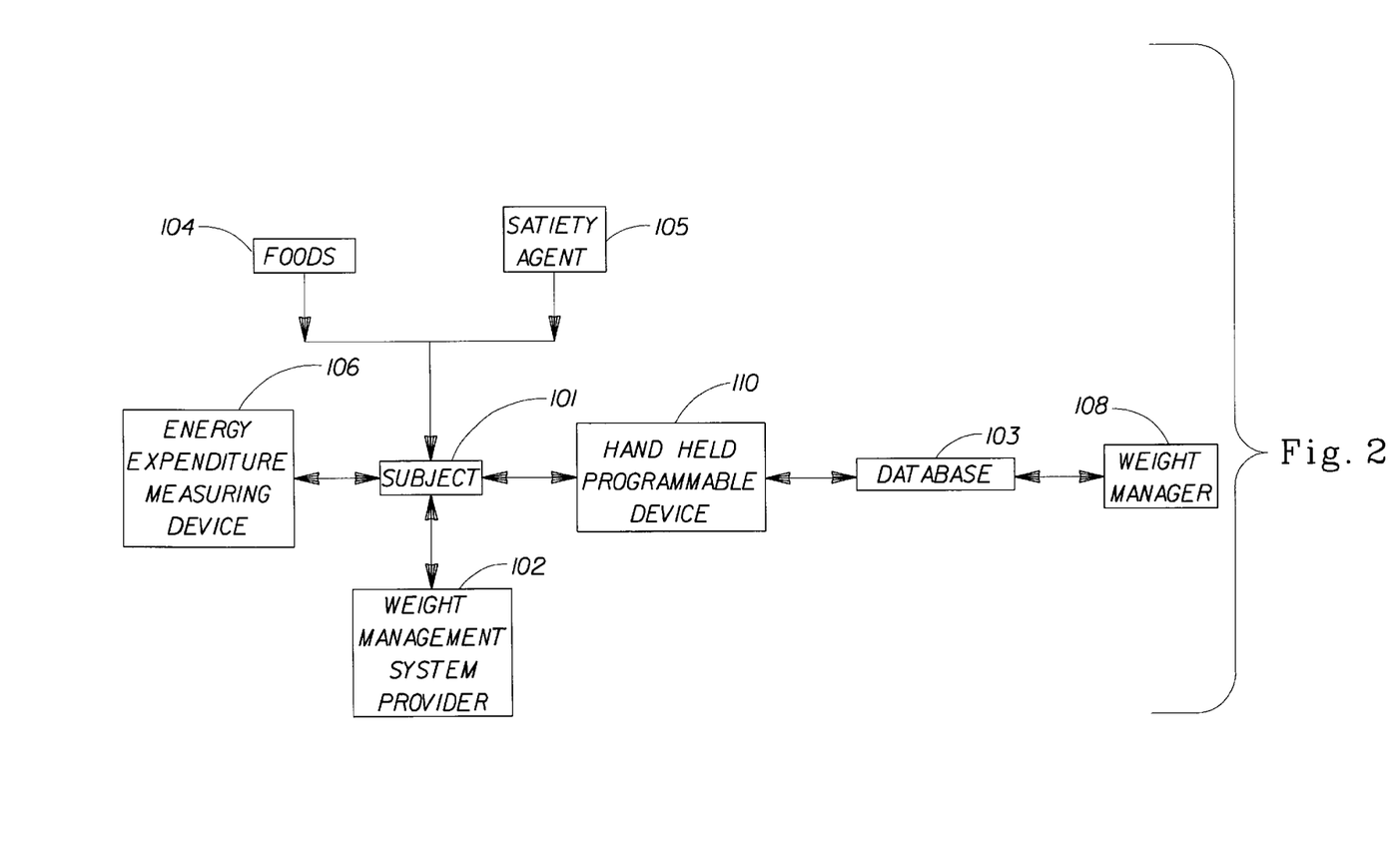
FIG. 2 shows the body weight management system of FIG. 1 wherein a hand held programmable device serves as the means for recording information in a database. The database is integral or separate from said hand held programmable device.

FIG. 2 shows a system according to FIG. 1 wherein a hand held programmable device 110 is employed. The hand held programmable device 110 is used wherein the diet-tracking system tool is in the form of software that is capable of being loaded onto the hand held programmable device 110. The subject creates the subject data profile in the software loaded into the hand held programmable device 110. Database 103 can remain separate from said programmable device or can be integrated within said programmable device.

Figure 3:
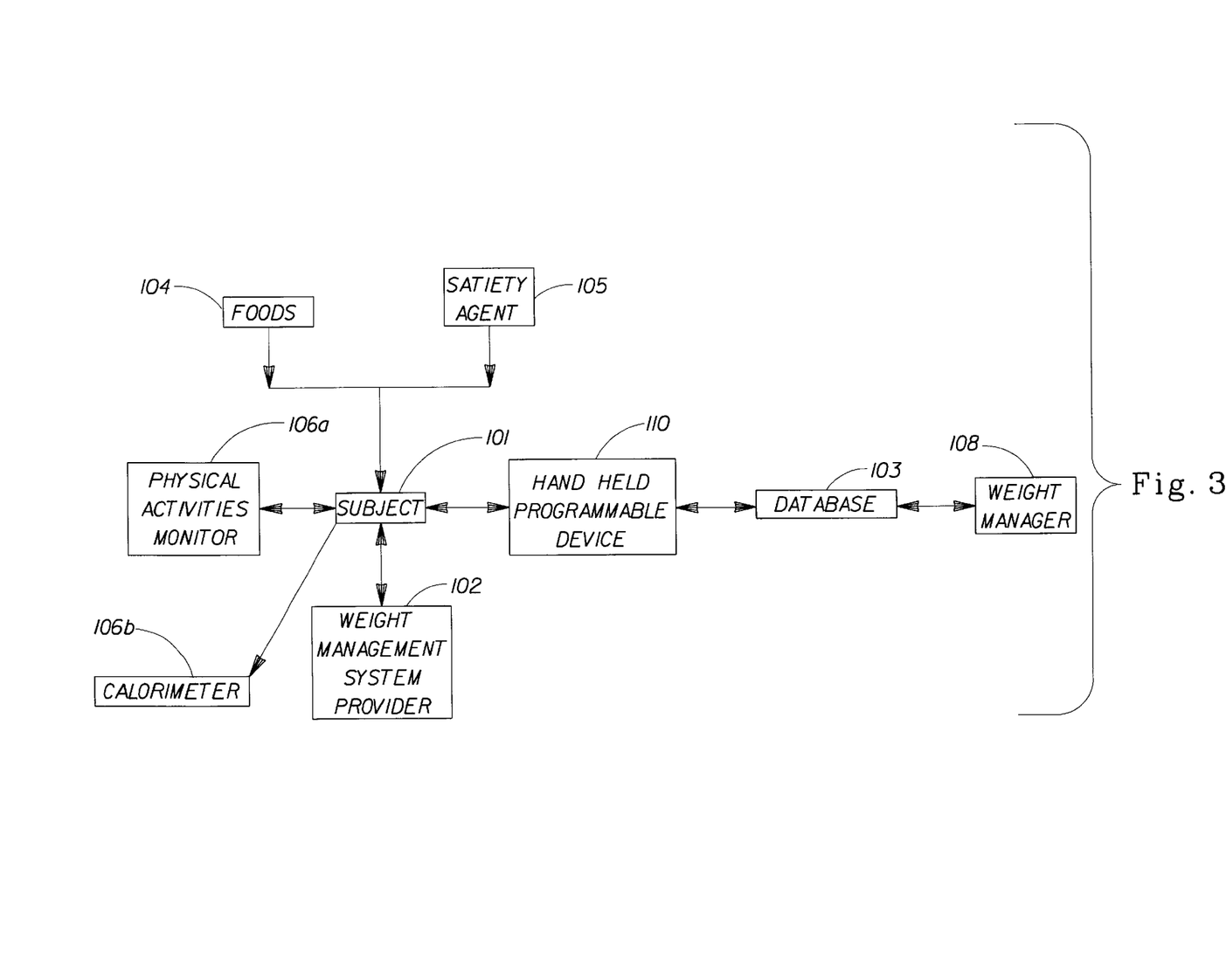
FIG. 3 shows the body weight management system of FIG. 3 employing a physical activity monitor and a calorimeter for estimating energy expenditure of the subject.

FIG. 3 shows a system according to FIG. 2 wherein the energy expenditure measuring device comprises physical activity monitor 106(a) and a calorimeter 106(b).

Figure 4:
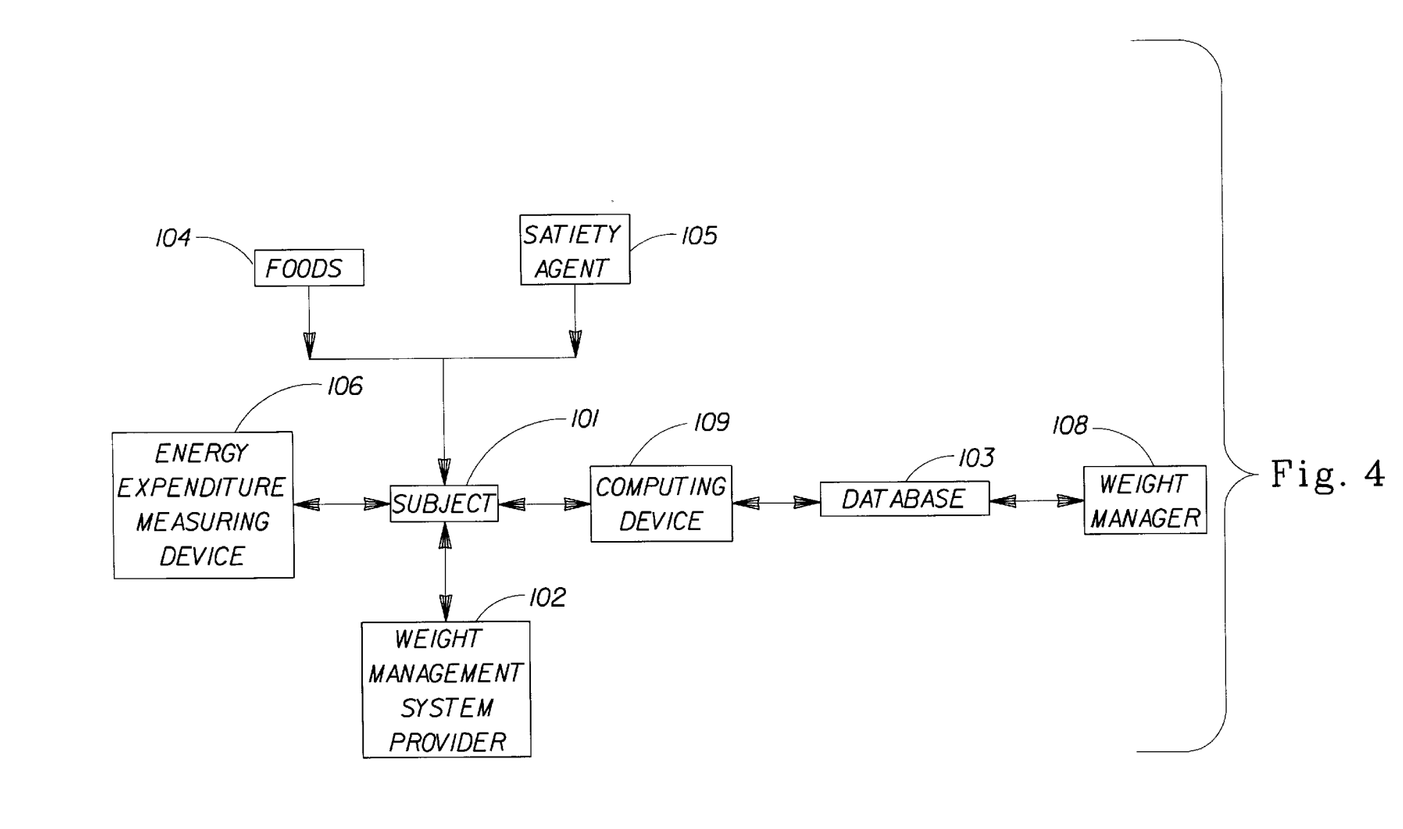
FIG. 4 shows the body weight management system of FIG. 1 wherein a computing device serves as the means for recording information in a database that is integral or separate from said computing device.

FIG. 4 shows a system according to FIG. 1 wherein a computing device is used. The computing device is used wherein the diet-tracking system tool is in the form of software and loaded onto the computing device 109 from floppy disc provider from the system provider 102. The subject creates the subject data profile in the software loaded into the computing device 109. Database 103 can remain separate from said computing device or can be integrated within the computing device.

Figure 5:
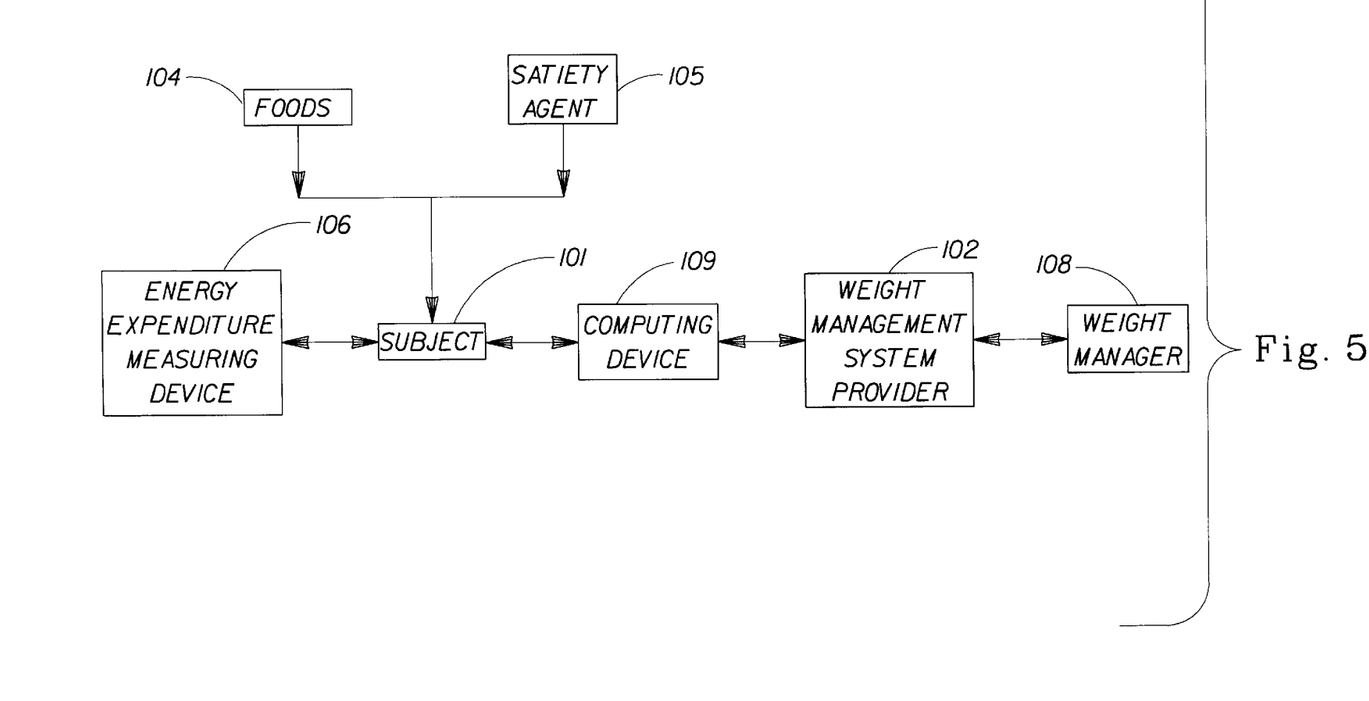
FIG. 5 shows the system of FIG. 4 wherein the subject transfers the energy balance data via his computing device by conventional communications channels to a weight management system provider. Said system provider transfers this data to a database wherein the database is accessible to the weight manager. The weight manager analyzes the data and provides information and, or feedback through the system provider back to the subject.

FIG. 5 shows a system wherein the computing device 103 of FIG. 2 wherein the computing device 103 is in communication with the system provider 102 using traditional means of communication including, but, not limited to mailings and, or telephonic forms of communication. The subject provides the energy balance data in the database contained in the computing device 103 to said system provider 102. Said system provider 102 makes the data from said database available to the weight manager 108. Said weight manager 108 analyzes said data and generates feedback to subject 101 to help the subject modifying the energy balance factors to maintain progress towards the body weight management goals established in the subject data profile.

Figure 6:
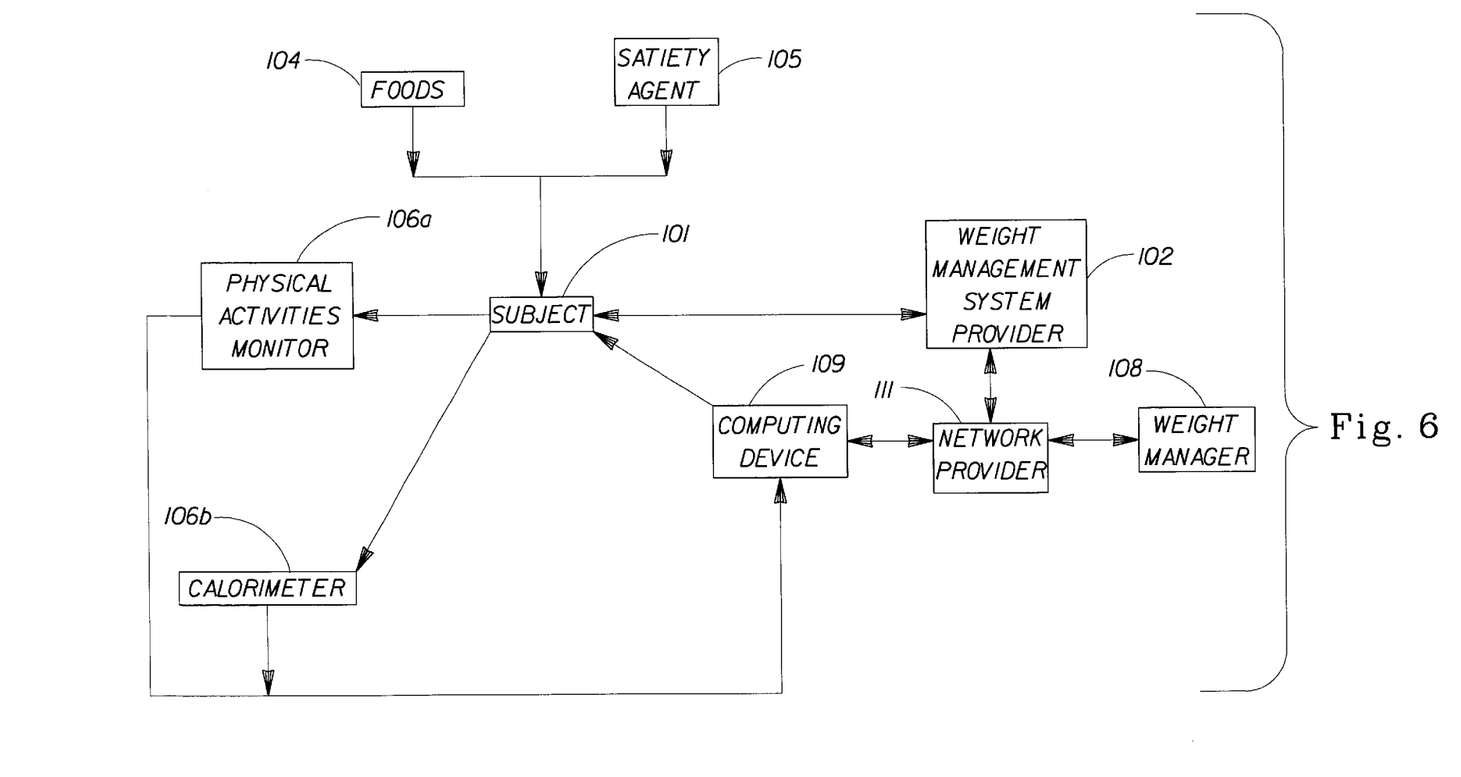
FIG. 6 shows a body weight management system in FIG. 5 wherein the computing device is in communication with the weight manager through a network provider. Said tools can be sent through the network provider as computer software programs. Said software programs may be downloaded onto computing device 109. Said body weight management system additionally comprises a calorimeter and a physical activity monitor to measure and record energy expenditure. Said devices are directly in communication with said computing device.

FIG. 6 shows a system wherein the computing device 103 of FIG. 2 wherein the computing device 103 is in communication with the weight manager 108 through a communication network 111 such as the Internet. The energy expenditure device comprises a physical activity monitor 106(a) and the calorimeter 106(b) wherein the said devices are in direct communication with the computing device 109. This allows the data accumulated by said devices to be entered directly from said devices to the database in said computing device 109. The data in said database in computing device 109 is transferable through the network provider 111. While said system provider 102 remains in communication with the subject 101, the system provider may also communicate with the user via the computing device 109. Furthermore, said system provider 102 may monitor the activities of the subject relative to the data provided to the weight manager 108 and the feedback to the subject through the system provider's connection to the network.

Figure 7:
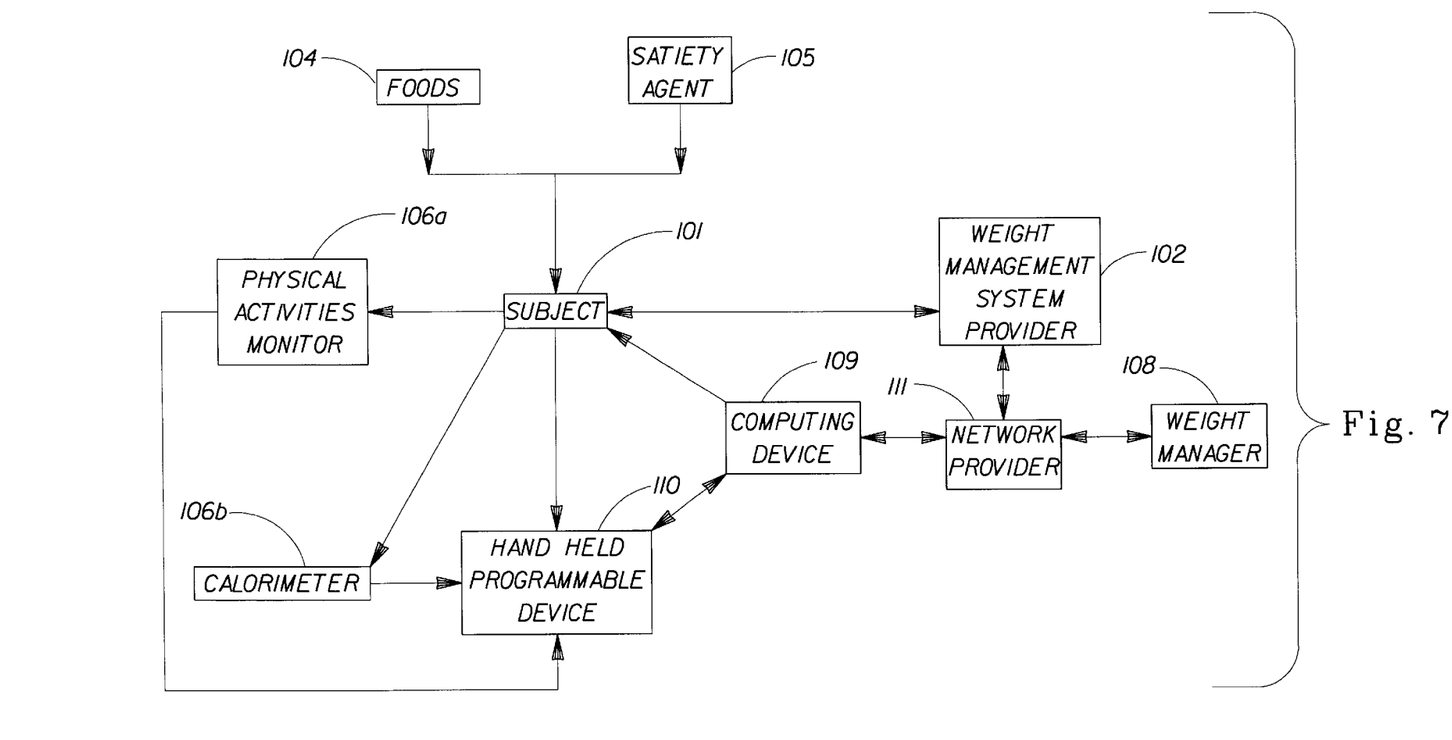
FIG. 7 shows a body weight management system in FIG. 6 additionally comprising a hand held programmable device for accepting the data from the user, the activity monitor and calorimeter. Said hand-held programmable device is in communication with said computing system.

FIG. 7 shows a body weight management system in FIG. 6 alternatively wherein the diet-tracking tool resides on the server for the network provider 111. Computing device 109 acts as a link from the subject 101 to the network provider 111, wherein subject may manipulate the tool rather than loading it into the computing device 109. FIG. 7 comprising a hand held programmable device for accepting the data directly from activity monitor 106(a) and calorimeter 106(b). The hand held programmable device 110 is in communication with the computing device 109 that is in tern in communication with the network provider 111 as discussed in FIG. 6 above.

Figure 8:
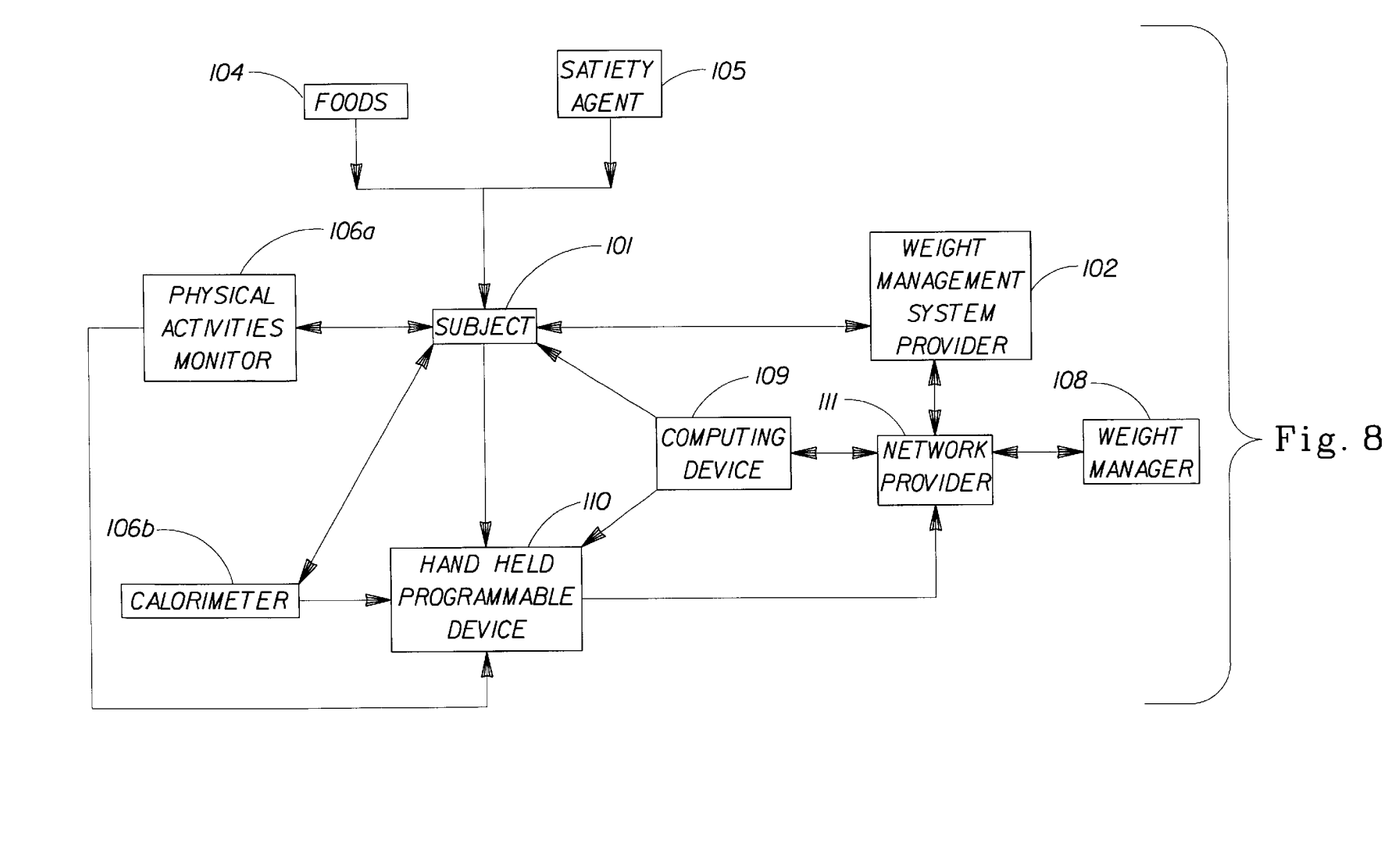
FIG. 8 shows a body weight management system of FIG. 4 wherein the hand held programmable device is in direct communication with the network provider and the feedback loops through the subject's computing device.

FIG. 8 shows a body weight management system as in FIG. 6 wherein the energy expenditure data from said devices 106(a) and 106(b) is collected by the hand held programmable device 110 and is transferred directly to the network by wireless transmission rather than through the computing device 109. Computing device 109, however, may receive the feedback from weight manager 108 through the network provider 111 to the computing device 109. Such feedback may be transferred to the hand held programmable device 110.

Method of Using the Body Weight Management System

There are a variety of methods for using the present invention. The selection of the method of use by the subject depends to a greater or lesser degree on the subject's ability to acquire and manipulate electronic equipment in order to ultimately communicate back and forth with the weight manager. The methods of using the body weight management system of the present invention include the following:

A method of using a present invention by the subject comprising the following steps:
 a. subscribing to said body weight management system through a weight management system provider;
 b. establishing a subject authenticating code with said system provider;

c. creating a journal for the subject to record the energy balance data of the subject;
d. recording in said journal the energy intake data associated with foods consumed employing the diet-tracking system tool provided by the body weight management system provider;
e. recording in said journal the energy expenditure data associated with physical activities as determined from the energy expenditure devices provided by said body weight management system provider; and
f. transferring said energy balance data to a weight manager for processing the data to develop feedback to said subject for modifying their consumption and, or exercise habits to meet the body weight management goals.

In an alternative method for using the present invention, the subject utilizes a computing device wherein the diet-tracking tool is in the form of software. In this embodiment, the subject loads this software on to his computing device or personal computer. Rather than creating a journal, the subject creates the subject data profile using the software and also records all data regarding energy intake and energy expenditures into the database created in the computing device. The subject transfers the data from the computing device to the weight manager, either directly or through the weigh management system provider. If transferred directly, the subject may use any means to do this including, but not limited to mailing the data in printed or electronic form. The data may also be transferred by electronic mail or through a network service provider. The data regarding the subject's energy balance may also be transferred to the weight manager in printed or electronic form. In an alternative embodiment of the present invention, the subject's data regarding energy balance is recorded and transferred automatically from a hand-held programmable device to the weight manager by wireless transmission.

The methods for body weight management of humans and other animal subjects using compositions of the present invention comprise the step of administration of said composition to the subject at a time prior to food consumption, during food consumption or as a replacement for food consumption and combinations thereof. Any food that is consumed by the subject concomitant with the composition preferably has a maximum triacylglycerol level of about 5 grams. When administered prior to food consumption, the period prior to consumption of food is sufficiently early enough to prevent substantial interaction with any triacylglycerol components of the food being consumed and to increase hepatic fatty acid β-oxidation and hepatic and celiac vagal activity during said consumption, leading to premature induction of satiety and reduction of energy intake during consumption. Said composition is also believed to be effective in a method for controlling the appetite of a subject.

Generally, administration of the composition of the present invention takes place from about 30 minutes to 6 hours prior to consumption of food. It is preferable that the composition be taken in this period, prior to the subject's primary meals of the day, usually before their morning, mid-day and evening meals. Administration of the composition of the present invention may also replace one or a plurality of the said subject's primary meal or meals.

Use of a calorimeter is also a component of the present system. As discussed above, a subject normally breathes into a calorimeter to a required period for the device to estimate the resting metabolic rate by the oxygen consumption rate detected by the device.

EXAMPLES

While particular embodiments of the preset invention are herein illustrated and described, light of the present application it would be obvious to those skilled in art that various other changes ad modifications can be made without departing from the spirit and scope of the invention.

Example 1

In anticipation of planning to attend a special event, a 45 year-old woman discovers that clothing previously worn to such an event no longer fits properly. In order to wear such clothing, she estimates she need to lose about 20 pounds over the next two to three months.

The woman or subject learns of the system of the present invention through an acquaintance and contacts the body weight management service provider by telephone. She subscribes to the body weight management system of the present invention. She selects an authenticating code with the service provider. The system provider accepts the woman's information subscription and sends her the system's tools. These tools, comprising a diet-tracking system that includes a journal or log, an energy expenditure-measuring device in the form of an indirect calorimeter and a two-month supply of a satiety product. The subject creates subject data profile or personal history and goes through a detailed set of questions designed to determine her body weight management goals.

The subject starts using the journal, recording her daily consumption of foods. The journal also contains tables that provide the caloric values of the foods at their portion size. The energy intake data from the consumed foods (in calories or points) may be entered into said journal. The subject also enters the values for the energy expenditure on a daily basis from the indirect calorimeter. The user breathes entirely through the indirect calorimeter for a sufficient period (about 5 minutes) to obtain an accurate reading of her resting metabolic rate. The subject also consumes sufficient quantity of the satiety product to shift the energy balance towards energy expenditure and away from energy intake, creating a deficit in terms of expending more calories than consumed on a daily basis.

The subject routinely sends the journal to the system provider who relays the information to a database. The database is made accessible to the weight manager. The weight manager analyzes the data and determines subject's energy balance. The weight manager determines the action steps the subject should take to meet the subject's body weight management goals as determined from the subject's data profile. This feedback is routed through the system provider. The system provider relays this feedback to the subject. Over the course of the two months, the subject and system manager exchange data and feedback. At the end of two months the subject has lost the weight necessary to fit into the clothing she desires. At this point, the subject may maintain the subscription to continue to manage her weight to remain consistently at the desired weight.

Example 2

While training for a national female body building contest, a 35 year-old woman competitor determines that her chances of winning her classification this year would be enhanced if she could lower her overall body fat content to under 10%. To do this she and her fitness coach determine that she should shift her energy balance sharply towards energy expenditure through rigorous free-weight training exercises design to accentuate muscle groups in her legs and upper back. Neither her trainer or she, however, are certain of how much reduction in energy intake will maximize her muscle building.

While shopping in a local drug store, the competitor finds the present invention on the shelf. She brings the product kit home after purchasing and reads the instruction booklet accompanying the kit. She telephones the body weight manager system provider and registers herself as a customer and establishes her PIN. She then downloads the diet-tracking software onto her personal computer and creates a subject data profile including her weight management system goals. She then reads the system use instructions in the form of a computer tutorial. Upon finishing, she activates and wears an activity monitor found in the kit. In this particular embodiment of the system, the activity monitor is band with a sensing device attached to the band that is worn over the area in the upper arm. Said monitor comprises sensors to read, analyze and store selected body functions including pulse rate, body temperature, heat loss rate, skin sweat level, movement accelerometer and other appropriate measures of energy expenditure. This monitor is worn for a period of time and eventually is synchronized to the personal computer to download this data into the software mentioned above. In addition to the activity monitoring, she enters into the software, data regarding her food consumed. This information is routed through the weight management system provider to a weight manager. The weight manager reviews the information and compares it to the weight management system goals and determines the next steps the competitor takes. In this situation the weight manager determines that the energy expenditure by the designed exercises is appropriate, however, the energy intake or food consumption needs to be reduced. The weight manager directs the competitor to consume the satiety product from the kit and provides a recommended energy intake range to be maintained by her. The competitor continues to use the system until she reaches her body weight management goals.

Example 3

A father and his son enter a three-legged race at his company's annual summer picnic. Although only 38 years old and just slightly overweight, the father and son finish last in the race. While the son urges him to enter another race, the father realizes his poor physical conditioning prevents him from participating. That evening while smoking a cigar and sipping brandy, the father decides to get in better shape for the upcoming fall softball tournament at work.

The father goes onto the Internet using his personal computer to find out about systems for improving this overall physical condition. He determines that the body weight management system of the present invention offers the most advantage to his particular circumstances. He clicks onto to the web address of the system provider of the present invention. He subscribes to the body weight management system of the present invention. He creates a PIN to access the database created for him in the network server by the system provider. The system provider also provides access the tools that the subject will use including an on-line diet-tracking system. The system provider will send to the subject energy expenditure devices including a physical activity monitor and a calorimeter as well as a supply of the satiety product comprising the satiety agent of the present invention. The subject enters this information through his computer into the diet-tracking network tool provided by the system provider. The subject also tracks his daily energy expenditure using the computer to enter his daily physical activity and metabolic rate into the database created for the subject in the network server. The database data is processed by a network computer and the information regarding the subject's energy balance is created and stored on the database. A system manager analyzes the data and determines that the subject has to reduce shift his energy balance and recommends that he reduce his daily energy intake by 10% while increasing his energy expenditure by 10% for a stated period. This advice or feedback is transmitted from the system manager through the network to the subject over his personal computer. The subject attempts to follow this advice. To assist in curbing his appetite to make the energy reduction of 10%, he consumes a sufficient amount of products comprising the satiety agents of the present invention.

Example 4

A 48 year old male goes on vacation in Washington D.C. While taking a walking tour of the monuments, he finds that he labors to keep up with the tour group of senior citizens. Upon returning home, he determines to lose weight and maintain a healthy life style.

The subject goes onto the Internet from his hand held programmable device such as a Palm Pilot® to find out about body weight management systems. He determines that the body weight management system of the present invention offers the most advantage to his particular circumstances. He clicks onto to the web address of the system provider of the present invention. He subscribes to the body weight management system of the present invention. He creates a PIN to access the database created for him in the network server by the system provider. The system provider also provides access the tools that the subject will use including diet-tracking system software, energy expenditure devices including a physical activity monitor and a calorimeter as well as a supply of the satiety product comprising the satiety agent of the present invention. The service provider sends over the Internet software tools including the diet-tracking software. Other tools, such as the energy expenditure monitoring devices are shipped to him.

The subject loads the diet-tracking software onto his hand-held device such as a Palm Pilot®. He tracks her food intake by selecting the foods that are already found into the software program, including their caloric values. With or in place of food, the user consumes the satiety agent to reduce the amount of food consumed. The user breathes entirely through the indirect calorimeter for a period sufficient to obtain an accurate reading of her metabolic rate (about 5 to 15 minutes). The subject's daily energy physical activity and metabolic rate are automatically entered directly into the hand held device and into a database created on the device. The hand held device contains a data processor wherein the subject's energy balance is created and stored on the database. The energy balance data is conveyed via the internet directly from the hand held device to the system manger for analysis. The system manager analyzes the data and determines that the subject may maintain his energy input, but must increase his energy expenditure by 10% for a stated period. This advice or feedback is transmitted from the system manager through the network to the subject over his personal computer. The subject attempts to follow this advice. To off-set the increased appetite due to the increased physical activity, the subject consumes a sufficient amount of products comprising the satiety agents of the present invention.

What is claimed is:

1. A body weight management system comprising:
    (a) a composition comprising a satiety agent selected from the group consisting of long chain fatty acids, their non-glyceryl esters, hydrolyzable in the presence of gastrointestinal enzymes, and mixtures thereof, wherein upon ingestion of the composition by a subject the satiety agent releases in the stomach of the subject;
    (b) a diet-tracking system, wherein the diet-tracking system is capable of estimating caloric intake of the subject over a first period of time and wherein at least a portion of the caloric intake is derived from ingestion of the composition by the subject;
    (c) an energy expenditure measuring device, wherein the energy expenditure measuring device is capable of estimating the expenditure of the caloric intake of the subject over a second period of time; and
    (d) a weight manager, wherein the weight manager is capable of communicating data to the subject, wherein the data is selected from the group consisting of information, feedback and combinations thereof and wherein at least a portion of the data is derived from an estimation created by the diet-tracking system or the energy expenditure measuring device.

2. The body weight management system according to claim 1, wherein the diet-tracking system is selected from the group consisting of manual tracking systems, software tracking systems, and combinations thereof.

3. The body weight management system according to claim 2 wherein the energy expenditure measuring device is selected from the group consisting of calorimeter devices, physical activity monitors, and combinations thereof.

4. The body weight management system according to claim 3 wherein the energy expenditure measuring device is an indirect calorimeter.

5. The body weight management system according to claim 4 wherein the indirect calorimeter comprises means for measurement of carbon dioxide present in respiratory gases of the subject.

6. The body weight management system according to claim 3 wherein the energy expenditure measuring device is a pedometer.

7. The body weight management system according to claim 1 wherein the long chain fatty acids contain a carbon chain length of from about 12 to about 24 and contain from 0 to about 6 carbon-carbon atom double bonds.

8. The body weight management system according to claim 7 wherein the long chain fatty acids are selected from the group consisting of lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linoleic acid, eleostearic acid, licanic acid, arachidonic acid, arachidic acid, eicosenoic acid, eicosapentaenoic acid, behenic acid, erucic acid, docosahexaenoic acid, lignoceric acid, and mixtures thereof.

9. The body weight management system according to claim 8 wherein the long chain fatty acids contain a carbon chain length of from about 16 to about 18 and contain from 0 to about 3 carbon-carbon atom double bonds.

10. The body weight management system according to claim 9 wherein the satiety agent is selected from the group consisting of oleic acid, linoleic acid, ethyl oleate, ethyl linoleate, and mixtures thereof.

11. The body weight management system according to claim 1 wherein the weight manager comprises means for estimating energy balance.

12. The body weight management system according to claim 11 wherein the data is communicated by a network provider to a computing device, wherein the computing device is accessible by the subject.

13. The body weight management system according to claim 11 wherein the data is communicated by means selected from the group consisting of portable media, hard wire, wireless transmission, and combinations thereof.

14. A body weight management system according to claim 1 which further comprises:
    (e) a weight management system provider; and
    (f) communication means capable of communication with at least one subject and the weight management system provider.

15. A method of managing body weight of a subject comprising:
    (a) ingesting a composition comprising a satiety agent selected from the group consisting of long chain fatty acids, their non-glyceryl esters, hydrolyzable in the presence of gastrointestinal enzymes, and mixtures thereof, wherein the satiety agent releases in the stomach of the subject;
    (b) employing a diet-tracking system, wherein the diet-tracking system is capable of estimating caloric intake of the subject over a first period of time and wherein at least a portion of the caloric intake is derived from the ingestion of the composition by the subject;
    (c) employing an energy expenditure measuring device, wherein the energy expenditure measuring device is capable of estimating the expenditure of the caloric intake of the subject over a second period of time; and
    (d) employing a weight manager, wherein the weight manager is capable of communicating data to the subject, wherein the data is selected from the group consisting of information, feedback and combinations thereof and wherein at least a portion of the data is derived from an estimation created by the diet-tracking system or the energy expenditure measuring device.

16. The method according to claim 15 wherein the data comprises energy balance data.

17. The method according to claim 16 further comprising communicating the data to the subject by means selected from the group consisting of electronic mail, network communication, wireless transmission, and combinations thereof.

* * * * *